US010052196B2

(12) United States Patent
Pugh et al.

(10) Patent No.: US 10,052,196 B2
(45) Date of Patent: *Aug. 21, 2018

(54) PROCESSOR CONTROLLED INTRAOCULAR LENS SYSTEM

(71) Applicant: Johnson & Johnson Vision Care, Inc., Jacksonville, FL (US)

(72) Inventors: Randall B. Pugh, Jacksonville, FL (US); Daniel B. Otts, Jacksonville, FL (US); Frederick A Flitsch, New Windsor, NY (US); Janet Plapp, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/504,408

(22) Filed: Oct. 1, 2014

(65) Prior Publication Data

US 2015/0142107 A1  May 21, 2015

Related U.S. Application Data

(63) Continuation of application No. 13/599,738, filed on Aug. 30, 2012.

(60) Provisional application No. 61/529,350, filed on Aug. 31, 2011.

(51) Int. Cl.
*A61F 2/16* (2006.01)
*G02B 3/14* (2006.01)
*G02B 26/00* (2006.01)
*G02C 7/04* (2006.01)

(Continued)

(52) U.S. Cl.
CPC .......... *A61F 2/1635* (2013.01); *A61F 2/1624* (2013.01); *A61F 2/1627* (2013.01); *G02B 3/14* (2013.01); *G02B 26/005* (2013.01); *G02C 7/04* (2013.01); *G02C 7/085* (2013.01); *A61F 2002/482* (2013.01); *A61F 2220/005* (2013.01);

(Continued)

(58) Field of Classification Search
None
See application file for complete search history.

(56) References Cited

U.S. PATENT DOCUMENTS 4,373,218 A * 2/1983 Schachar .................. 623/6.13
5,712,721 A   1/1998 Large
6,855,164 B2  2/2005 Glazier (Continued)

FOREIGN PATENT DOCUMENTS

RU   2286750 C1  11/2006
SG    185541 A1  12/2012

(Continued)

OTHER PUBLICATIONS

International Search Report for PCT PCT/US2012/053068 dated Nov. 26, 2012.

(Continued)

*Primary Examiner* — Leslie Lopez

(57) ABSTRACT

The present invention relates generally to an intraocular lens system controlled with a processor, including a liquid meniscus lens and supporting electronics. Embodiments may include intraocular lens systems of various shapes and sizes, liquid meniscus lens components of various shapes and sizes, variations in supporting electronics with corresponding variations in lens function.

28 Claims, 7 Drawing Sheets

(51) Int. Cl.
   *G02C 7/08* (2006.01)
   *A61F 2/48* (2006.01)
(52) U.S. Cl.
   CPC ............... *A61F 2230/0004* (2013.01); *A61F 2250/0043* (2013.01)

(56) References Cited

U.S. PATENT DOCUMENTS

| | | |
|---|---|---|
| 7,311,398 B2 | 12/2007 | Kuiper et al. |
| 7,327,523 B2 | 2/2008 | Tanaka |
| 7,857,850 B2 | 12/2010 | Mentak et al. |
| 8,526,113 B2 | 9/2013 | Pugh et al. |
| 8,634,145 B2 | 1/2014 | Pugh et al. |
| 8,638,501 B2 | 1/2014 | Pugh et al. |
| 8,638,502 B2 | 1/2014 | Pugh et al. |
| 8,665,526 B2 | 3/2014 | Pugh et al. |
| 2004/0117011 A1 | 6/2004 | Aharoni |
| 2005/0071002 A1* | 3/2005 | Glazier ............ 623/6.13 |
| 2005/0200973 A1 | 9/2005 | Kogo et al. |
| 2007/0100443 A1* | 5/2007 | Peyman ............ 623/6.13 |
| 2007/0153405 A1* | 7/2007 | Kuiper et al. ........ 359/846 |
| 2009/0204207 A1 | 8/2009 | Blum |
| 2009/0244477 A1* | 10/2009 | Pugh et al. ........ 351/158 |
| 2009/0264966 A1 | 10/2009 | Blum |
| 2010/0020285 A1 | 1/2010 | Berge |
| 2010/0110372 A1* | 5/2010 | Pugh ............ B29D 11/00009 351/159.75 |
| 2010/0149651 A1 | 6/2010 | Berge et al. |
| 2012/0310339 A1 | 12/2012 | Berge |

FOREIGN PATENT DOCUMENTS

| | | |
|---|---|---|
| WO | WO 2005088388 A1 | 9/2005 |
| WO | WO 2007020184 A1 | 2/2007 |
| WO | WO 2007/107589 A1 * | 9/2007 ............ A61F 2/16 |
| WO | WO 2007107589 A1 | 9/2007 |
| WO | WO 2010051203 | 5/2010 |
| WO | WO 2011143554 A1 | 11/2011 |

OTHER PUBLICATIONS

Singapore Search Report, Written Opinion for Application No. 2014012223—Invitation to Respond dated May 28 2015.
Vdovin G: "On the possibility of intraocular adaptive optics", Optics Express, OSA (Optical Society of America), Washington DC, (US), vol. 11, No. 7, Apr. 7, 2003 (Apr. 7, 2003), pp. 810-817, XP002323798, ISSN: 1094-4087, 001: 10.1364/0E.11.000810.

* cited by examiner

 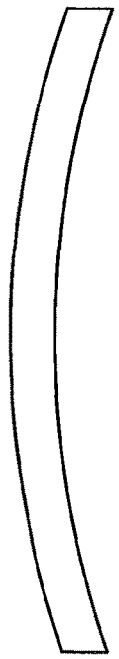 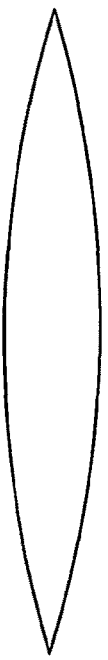
Fig. 6A  Fig. 6B  Fig. 6C
FIG. 6

PROCESSOR CONTROLLED INTRAOCULAR LENS SYSTEM

CROSS REFERENCE TO RELATED APPLICATIONS

The present application is a continuation of U.S. patent application Ser. No. 13/599,738, filed Aug. 30, 2012; which claims priority to Provisional Patent Application 61/529,350, filed on Aug. 31, 2011 "; the contents of which are relied upon and incorporated by reference

FIELD OF USE

The present invention relates generally to an intraocular lens controlled with a processor. Some specific embodiments include an intraocular lens with a liquid meniscus.

BACKGROUND

Since the mid-$20^{th}$ century, intraocular lenses (IOLs) have been implanted in eyes, replacing a patient's natural crystalline lens that is clouded by cataracts or changing the eye's optical power. Initially, IOLs were fixed monofocal lenses of a power to provide correction only for distance vision. Even today, a majority of IOLs implanted during eye surgery are monofocal, requiring a patient to wear glasses for near vision correction.

More recent advances have included multifocal IOLs which provide a patient with correction for both distance and near vision. Multifocal IOLs employ the same technology as multifocal contact lenses, but implemented within an intraocular lens.

Some IOLs currently claim adaptive capabilities, providing the patient with limited visual accommodation. Accommodating IOLs are designed to allow the eye to shift focus onto near objects. Current versions of accommodating IOLs rely on physical changes within the eye to effect a change in the shape of an intraocular lens, resulting in a change in the lens' optical power. In many implementations, the optical properties of accommodating IOLs cannot be changed after implantation, although such changes may be desirable for a variety of reasons. In many cases, a patient's vision prescription changes as a result of the eye surgery necessary to implant the IOL. The closure and healing of the incision may induce astigmatism as portions of the eye are drawn together to close the incision. Further, as a patient ages and ciliary muscles within the eyes weaken, the eyes are no longer able to exert the necessary force to change an IOL's shape and achieve the desired level of accommodation. Finally, even a minor error in the initial IOL prescription will leave the patient with less than optimal vision.

More recently, it has been theorized that electronic components may be incorporated into an intraocular lens. Electronic components may enable an intraocular lens including a liquid meniscus lens which provides variable focus that can be controlled and adjusted in a variety of ways.

SUMMARY

Accordingly, the present invention provides an intraocular lens system controlled with a processor, including a liquid meniscus lens and supporting electronics.

According to the present invention, an intraocular lens system includes an optical zone in which is found a liquid meniscus lens, and an electrical zone with components such as power sources, processors, memory, sensors, and communication elements. Power sources within an intraocular lens system may be recharged or receive continuous charge using a variety of methods. The liquid meniscus lens, supported by power sources, sensors and logic within the intraocular lens system, provides automated or manual focus capabilities, providing focus for near vision, far vision, and points in between. After surgical insertion, various capabilities of an intraocular lens system may be remotely adjusted, such as to correct for surgery-induced astigmatism, to adjust sensitivity of lens functions to changes in sensor data, and to alter the range of diopter correction between far and near vision.

DESCRIPTION OF THE DRAWINGS

FIGS. 6A, 6B and 6C illustrate various cross-sectional side views of an exemplary intraocular lens system according to some embodiments of the present invention.

DETAILED DESCRIPTION OF THE INVENTION

Figure 1A:
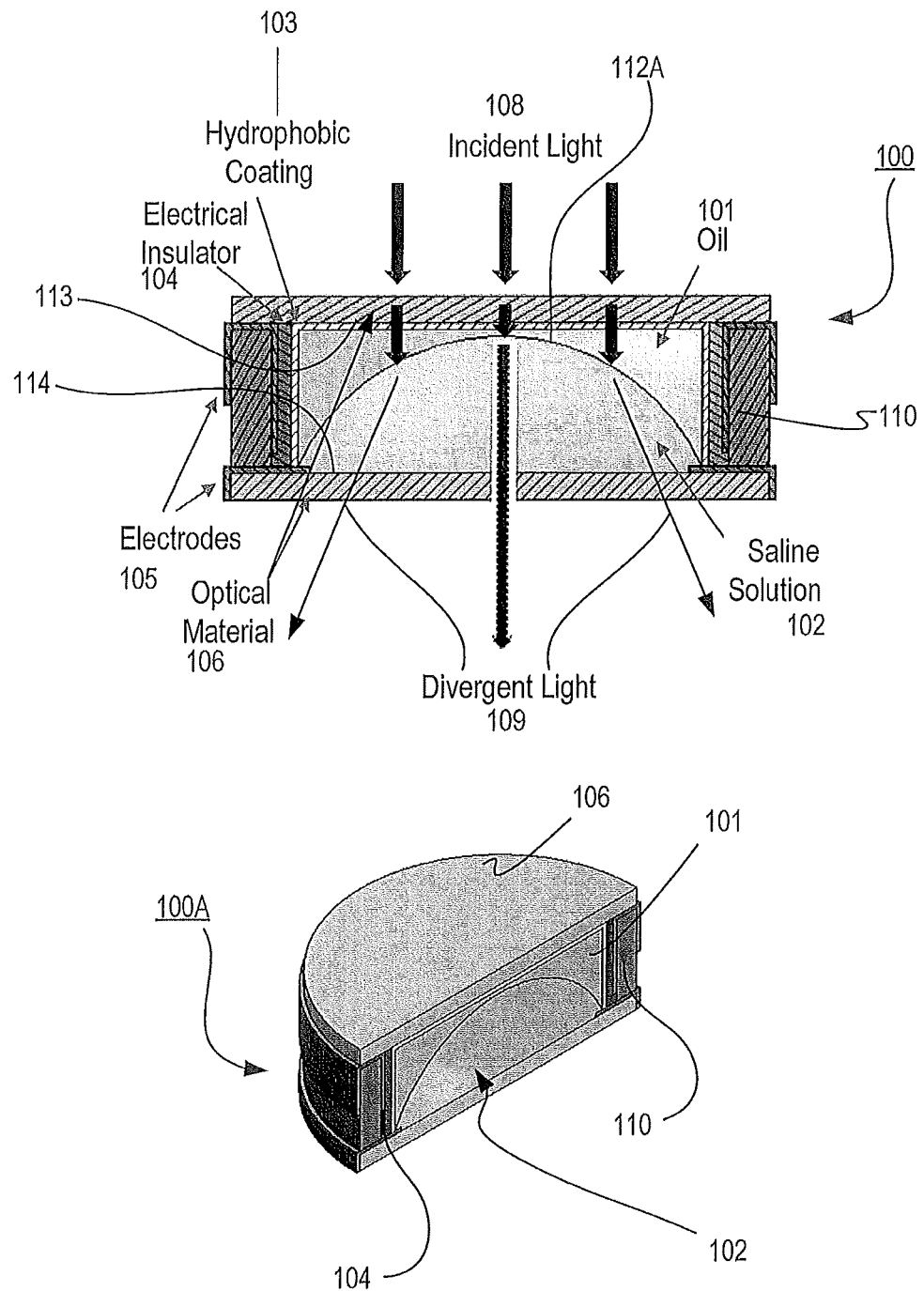
FIG. 1A illustrates a prior art example of a cylindrical liquid meniscus lens in a first state.

The present invention includes methods and apparatus for forming an intraocular lens system controlled by a processor. In particular, the present invention includes methods and apparatus for providing an intraocular lens system controlled by a processor, including a liquid meniscus lens and supporting electronics. In some embodiments, the present invention includes a liquid meniscus lens in an optic zone with supporting electronics located in an electrical zone around the periphery.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

Glossary

In this description and claims directed to the presented invention, various terms may be used for which the following definitions will apply:

Accommodation (and Accommodating IOL): as used herein refers to the process by which the eye changes optical power to maintain a clear image (focus) on an object as its distance changes.

Astigmatism: as used herein refers to faulty vision resulting from defective curvature of the cornea or lens of the eye.

Capsular Bag: as used herein refers to a sack-like structure remaining within the eye following removal of the natural lens. An implanted intraocular lens is placed within this structure to recreate the usual phakic (presence of the natural crystalline lens) state.

Ciliary Muscle: as used herein refers to a ring of striated smooth muscle in the eye's middle layer (vascular layer) that controls accommodation for viewing objects at varying distances.

Diopter: as used herein refers to a unit of measure of the optical or refractive power of a lens.

Electrical Zone: as used herein refers to an area around the periphery of an optical zone in which electronic elements are found.

Intraocular Lens System: as used herein refers to an intraocular lens including supporting electronics and a liquid meniscus lens.

Intraocular Lens (IOL): as used herein refers to an implanted lens in the eye, usually replacing the existing crystalline lens because it has been clouded over by a cataract, or as a form of refractive surgery to change the eye's optical power.

Liquid Meniscus Lens: as used herein refers to a lens containing one or more fluids to create an infinitely-variable lens without any moving parts by controlling the meniscus (the surface of the liquid.)

Microprocessor: as used herein refers to a circuit or series of circuits capable of receiving digital data and performing a calculation based upon the data received.

Monofocal Lens: as used herein refers to a lens with a fixed focus for one distance.

Multifocal Lens: as used herein refers to a lens that has rings of focus power variations. Some rings provide focus for near objects, some for mid-range objects, and some rings provide the focus power for distant objects.

Optical Zone: as used herein refers to an area of an ophthalmic lens through which a wearer of the ophthalmic lens sees. An ophthalmic lens may include a contact lens or an intraocular lens.

Referring now to FIG. 1A, a cut away view of a prior art liquid meniscus lens 100 is illustrated with an oil 101 and a saline solution 102 contained within cylinder 110. The cylinder 110 includes two plates of optical material 106. Each plate 106 includes a flat interior surface 113-114. The cylinder 110 includes an interior surface that is essentially rotationally symmetric. In some prior art embodiments, one or more surfaces may include a hydrophobic coating 103. Electrodes 105 are also included on or about the perimeter of the cylinder. An electrical insulator 104 may also be used proximate to the electrodes 105.

According to the prior art, each of the interior surfaces 113-114 is essentially flat or planar. An interface surface 112A is defined between the saline solution 102 and the oil 101. As illustrated in FIG. 1A, the shape of the interface 112A is combined with the refractive index properties of the saline solution 102 and the oil 101 to receive incident light 108 through a first interior surface 113 and provide divergent light 109 through a second interior surface 114. The shape of the interface surface between the oil 101 and the saline solution 102 may be altered with the application of an electrical current to the electrodes 105.

FIG. 1A illustrates a perspective view of the prior art liquid meniscus lens illustrated at 100.

Figure 1B:
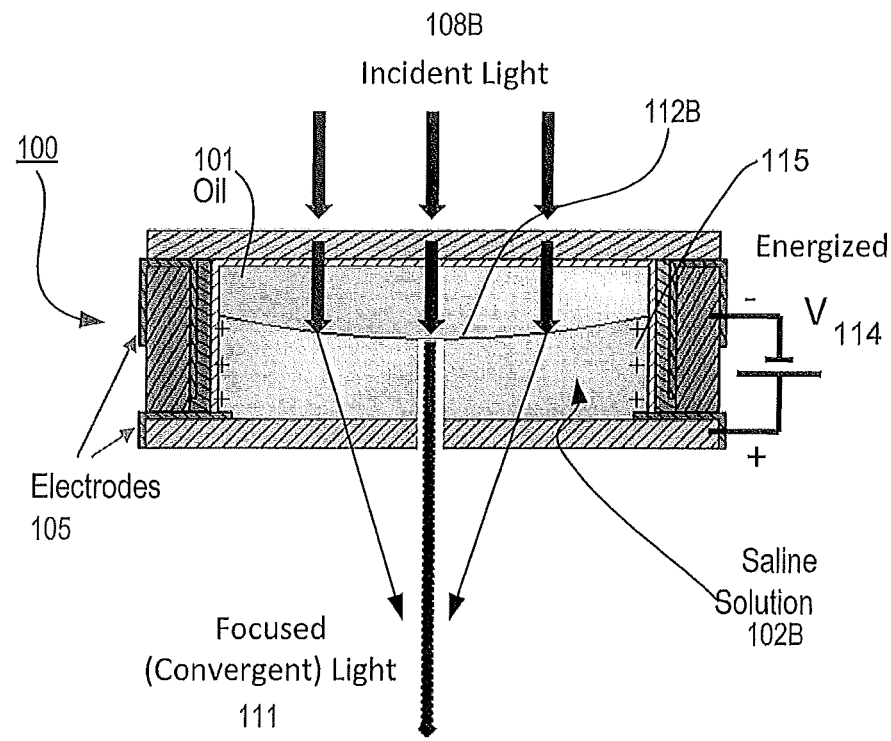
FIG. 1B illustrates the prior art example of a cylindrical liquid meniscus lens in a second state.
Figure 1B:
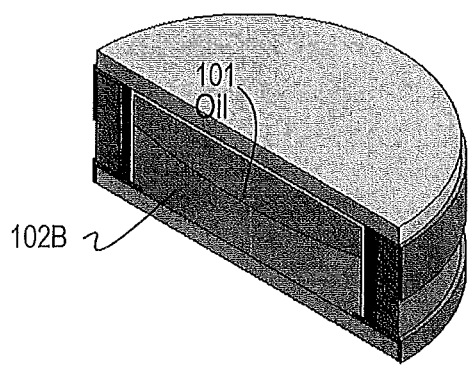

Referring now to FIG. 1B, the prior art liquid meniscus lens 100 is illustrated in an energized state. The energized state is accomplished by applying voltage 114 across the electrodes 105, exemplary voltages include, for example, between about 18.0 volts to 22.0 volts, between about 3.5 volts to about 7.5 volts, about 20 volts, and about 5 volts. The shape of the interface surface 112B between the oil 101 and the saline solution 102B is altered with the application of an electrical current to the electrodes 105. As illustrated in FIG. 1B, incident light 108B passing through the oil 101 and the saline solution 102B is focused into a convergent light pattern 111.

Figure 2:
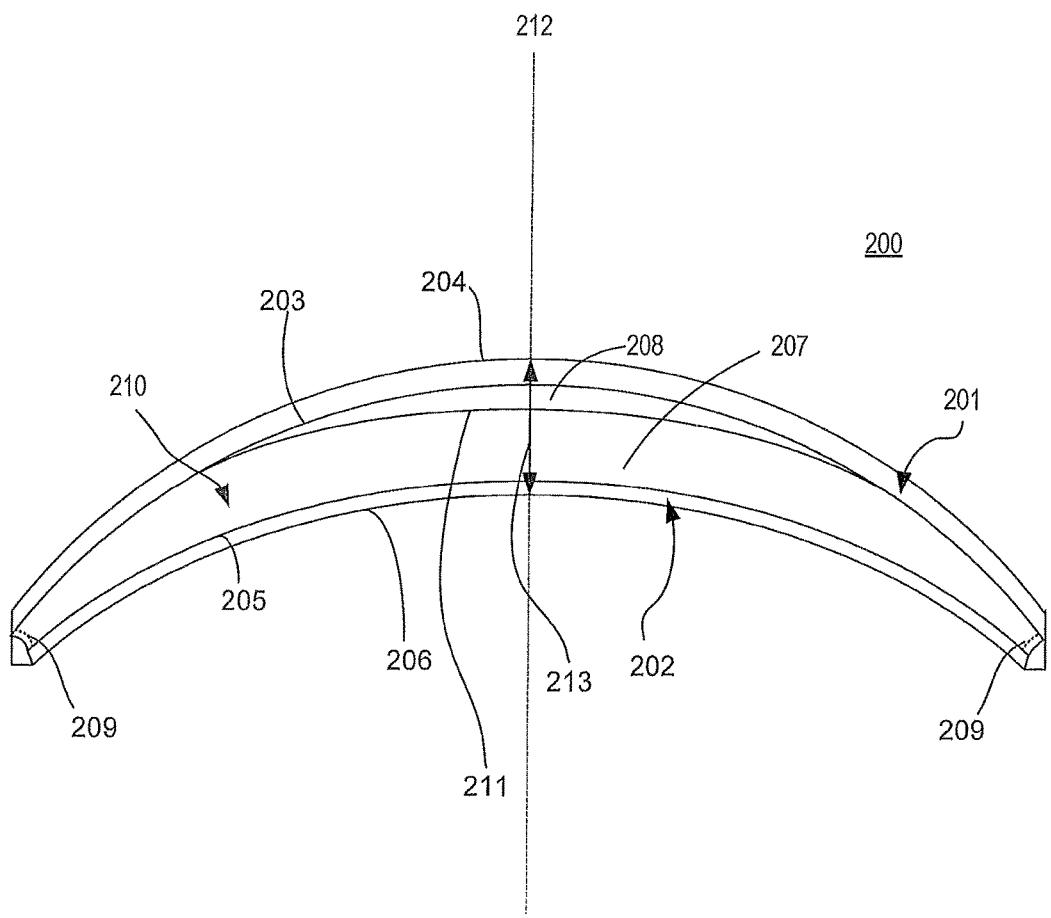
FIG. 2 illustrates a profile sliced cut away of an exemplary arcuate liquid meniscus lens according to some embodiments of the present invention.

Referring now to FIG. 2, a cut away view of a liquid meniscus lens 200 with a front curve lens 201 and a back curve lens 202. The front curve lens 201 and the back curve lens 202 are positioned proximate to each other and form a cavity 210 therebetween. The front curve lens 201 includes a concave arcuate interior lens surface 203 and a convex arcuate exterior lens surface 204. The concave arcuate lens surface 203 may have one or more coatings (not illustrated in FIG. 2). Coatings may include, for example, one or more of electrically conductive materials or electrically insulating materials, hydrophobic materials or hydrophilic materials, exemplary coatings may include Parylene C and Teflon® AF. One or both of the concave arcuate lens surface 203 and the coatings are in liquid and optical communication with an oil 208 contained within the cavity 210. The insulator may comprise a boundary area to maintain separation between the conductive coating and a saline solution contained in the cavity between the front curve lens and the back curve lens.

The back curve lens 202 includes a convex arcuate interior lens surface 205 and a concave arcuate exterior lens surface 206. The convex arcuate lens surface 205 may have one or more coatings (not illustrated in FIG. 2). Coatings may include, for example, one or more of electrically conductive materials or electrically insulating materials, hydrophobic materials or hydrophilic materials. At least one of the convex arcuate lens surface 205 and the coatings are in liquid and optical communication with a saline solution 207 contained within the cavity 210. The saline solution 207 includes one or more salts or other components which are electrically conductive and as such may be either attracted to or repulsed by an electric charge.

According to the present invention, an electrically conductive coating 209 is located along at least a portion of a periphery of one or both of the front curve lens 201 and the back curve lens 202. The electrically conductive coating 209 may include gold or silver and is preferably biocompatible. The conductive coating may extend from an area interior to the cavity to an area external to the cavity, and having an electrical terminal for providing an electrical charge to the conductive coating based upon a signal from a processor. In one embodiment, a channel through one or both of the front curve lens and the back curve lens contains a conductive material which may in addition have a terminal in electrical communication with the conductive material.

Application of an electrical charge to the electrically conductive coating 209 or electrical terminal creates either an attraction or a repulsion of the electrically conductive salts or other components in the saline solution 207. In some embodiments, the electrical charge comprises a direct current.

The front curve lens 201 has an optical power in relation to light passing through the concave arcuate interior lens surface 203 and a convex arcuate exterior lens surface 204. In some embodiments the front curve lens 201 exterior surface 204 comprises an optical power other than about 0 diopters. In some embodiments, the front curve lens 201 interior surface 203 comprises an optical power other than about 0 diopters. The optical power may be 0 or may be a plus or minus power. In some preferred embodiments, the optical power is a power typically found in corrective contact lenses or an artificial intraocular lens, such as, by way of non-limiting example, a power between −8.0 and +8.0 diopters.

The back curve lens 202 has an optical power in relation to light passing through the convex arcuate interior lens surface 205 and a concave arcuate exterior lens surface 206. In some embodiments, the back curve lens 202 interior surface 205 comprises an optical power other than about 0 diopters. The optical power may be 0 or may be a plus or minus power. In some embodiments, the optical power is a power typically found in corrective contact lenses or an artificial intraocular lens, such as, by way of non-limiting example, a power between −8.0 and +8.0 diopters.

Various embodiments may also include a change in optical power associated with a change in shape of a liquid meniscus 211 formed between the saline solution 207 and the oil 208. In some embodiments, a change in optical power may be relatively small, such as, for example, a change of between 0 to 2.0 diopters of change. In other embodiments, a change in optical power associated with a change in shape of a liquid meniscus may be up to about 30 or more diopters of change. Generally, a higher change in optical power associated with a change in shape of a liquid meniscus 211 is associated with a relatively thicker lens thickness 213.

According to some embodiments of the present invention, such as those embodiments that may be included in an ophthalmic lens, such as a contact lens or an intraocular lens, a cross cut lens thickness 213 of an arcuate liquid meniscus lens 200 will be up to about 1,000 microns thick. An exemplary lens thickness 213 of a relatively thinner lens 200 may be up to about 200 microns thick. Preferred embodiments may include a liquid meniscus lens 200 with a lens thickness 213 of about 600 microns thick. Generally a cross cut thickness of front curve lens 201 may be between about 35 microns to about 200 microns and a cross cut thickness of a back curve lens 202 may also be between about 35 microns and 200 microns.

According to the present invention, an aggregate optical power is an aggregate of optical powers of the front curve lens 201, the back curve lens 202 and a liquid meniscus 211 formed between the oil 208 and the saline solution 207. In some embodiments, an optical power of the lens 200 will also include a difference in refractive index as between one or more of the front curve lens 201, the back curve lens 202, oil 208 and the saline solution 207.

In those embodiments that include an arcuate liquid meniscus lens 200 incorporated into an ophthalmic lens, such as an intraocular lens and a contact lens it is additionally desirous for the saline 207 and oil 208 to remain stable in their relative positions within the arcuate liquid meniscus lens 200 as a wearer moves. Generally, it is preferred to prevent the oil 208 from floating and moving relative to the saline 207 when the wearer moves, accordingly, an oil 208 and saline solution 207 combination is preferably selected with a same or similar density. Additionally, an oil 208 and a saline solution 207 preferably have relatively low immiscibility so that the saline solution 207 and oil 208 will not mix.

In some preferred embodiments, a volume of saline solution 207 contained within the cavity 210 is greater than the volume of oil 208 contained within the cavity 210. Additionally, some preferred embodiments include the saline solution 207 in contact with essentially an entirety of an interior surface 205 of the back curve lens 202. Some embodiments may include a volume of oil 208 that is about 66% or more by volume as compared to an amount of saline solution 207. Some additional embodiments may include an arcuate liquid meniscus lens 200 wherein a volume of oil 208 is about 90% or less by volume as compared to an amount of saline solution 207.

Figure 3:
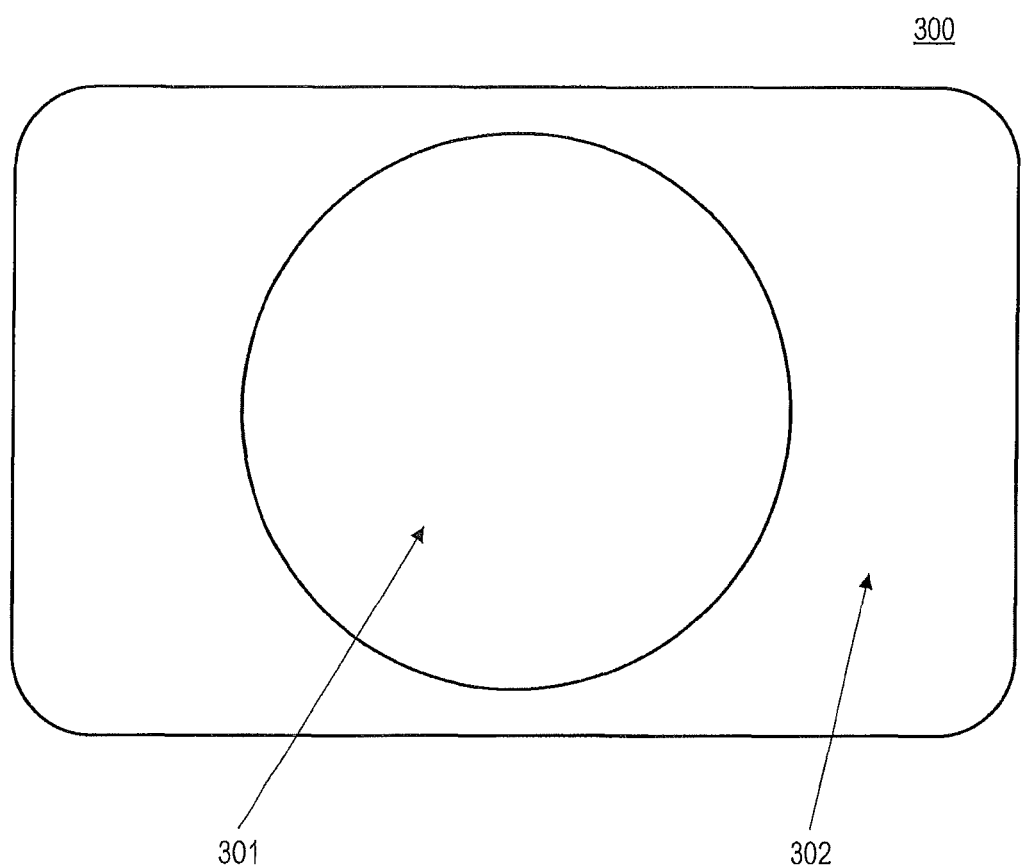
FIG. 3 illustrates a front view block diagram of an exemplary intraocular lens system in the form of a rounded rectangle according to some embodiments of the present invention.

Referring now to FIG. 3, depicted is a front view block diagram of an intraocular lens system 300 with an optical zone 301 surrounded by an electrical zone 302. In this embodiment, the intraocular lens system 300 is in the shape of a rounded rectangle with a circular visual zone 301 in the center. Other embodiments may include an optical zone 301 of elliptical, rectangular, or other shape conducive to vision correction. In the present invention, the visual zone 301 consists of a liquid meniscus lens. A liquid meniscus lens may be in a traditional "hockey puck" form, as described in FIGS. 1A and 1B, or in an arcuate form, as described in FIG. 2.

Around a perimeter of an optical zone 301 is an electrical zone 302 with supporting components for operation and control of an intraocular lens system with a liquid meniscus lens. In some embodiments, electrical zone 302 areas may be folded to facilitate insertion of the intraocular lens system into the eye during surgery. In preferred embodiments, an intraocular lens system may be encapsulated, in part or in whole, providing protection for supporting electronics and other sensitive components. Encapsulation may be accomplished, by way of illustrative example, via one or more known flexible materials such as silicone, silicone elastomer, silicone hydrogel, or flourohydrogel.

Some preferred embodiments of the present invention include within an electrical zone 302 self-contained power sources which autonomously power an intraocular lens system with liquid meniscus lens. In this case, self-contained power sources may be recharged infrequently, such as only at night, or only every few days. In some alternative embodiments, power sources are not self-contained, but are continuously or regularly recharged. Power sources may include, for example, one or more batteries or other storage devices. In some preferred embodiments, the storage devices include one or more lithium ion batteries or other rechargeable devices. Multiple power sources may be in an array and may include redundant elements to maximize the possibility of fail-safe operation.

Power sources may be charged by receiving and storing energy for current or future use. Nighttime charging, or charging while a user is sleeping, may be accomplished in a variety of ways. In a preferred embodiment, the user wears a sleep mask that emits a radio frequency or magnetic field for charging. This embodiment may be especially desirable in the case of radio frequency charging wherein radio frequency coils must be properly aligned with features on the intraocular lens system to achieve charging. A sleep mask maintains consistent alignment relative to a user's eyes as the user moves during sleep. In another embodiment, charging elements may be in temporary patches placed on a user's body during sleep, such as on their temple, forehead or cheekbone. If patches are placed on a user's head, they offer the benefit of consistent alignment with intraocular lenses, similar to a sleep mask. Other embodiments for sleep charging include a charging device contained in a pillowcase, a pillow, a blanket, or other article on which or near which a user sleeps. Additionally, far field charging may be accomplished by placing a charging device, such as radio frequency emitter, on a user's nightstand or headboard.

In some embodiments, wake-time charging is achieved with charging elements located in a user's eyeglasses or sunglasses frame emitting radio frequency or magnetic field. In other embodiments, continuous charging may be accomplished with photo sensors in an electrical zone 302 of an intraocular lens system. In this embodiment, light received by photo sensors is converted to electrical energy and stored in power sources within the electrical zone 302. Light for photo sensor charging may be in the visible spectrum or outside the visible spectrum. In yet another embodiment, a thermoelectric method may enable continuous charging or trickle charging of power sources. For example a temperature between the body temperature and an ambient temperature may be used to generate a trickle charge and harvested energy is stored in power sources within the electrical zone 302.

Charging of power sources may be via one or a combination of the various methods which have been described. One example of combined charging methods includes radio frequency charging during sleep cycles coupled with photo sensor trickle charging during wake cycles.

Some embodiments of the present invention include a power management subsystem supported by processor, memory and other components in an electrical zone 302 of an intraocular lens system with liquid meniscus lens, a wireless transmitter for communicating logic to and from the processor may also be incorporated. A power management subsystem may perform various functions, such as, for example, monitoring power usage and levels, managing the charging of power sources, limiting lens functions when power levels are below a minimum threshold, switching to draw power from one or more redundant power sources when others fail or fall below a specified threshold, and monitoring power sources to determine when charging is complete so that charging can be terminated.

Power sources supply electrical current to a liquid meniscus lens contained within an optical zone 301 of an intraocular lens system, wherein a change in the shape of the liquid meniscus results in a change in optical power, as described in FIG. 2. After receiving power, the liquid meniscus lens acts as a capacitor, holding a charge and maintaining an activated position of the liquid meniscus, such as increased optical power for near vision, without the continuous application of power. To revert to distance vision, power is discharged from the liquid meniscus lens and the liquid meniscus assumes its relaxed position, providing the appropriate default optical power for distance vision.

Power sources are under control of a microprocessor located within an electrical zone 302. The microprocessor executes one or more programs that analyze data and apply power accordingly to control operation of the intraocular lens system with liquid meniscus lens. In some embodiments, data analyzed by the microprocessor is in the form of sensed data, such as, for example, sensing contraction within the capsular bag, sensing a potential voltage change across a ciliary muscle, and sensing patterns of eyelid closing or squinting which signify an intent to switch between near and distance vision. Contraction of the capsular bag may be sensed, for example, via a pressure transducer. The transducer will translate a pressure change into one or both of an analog voltage or a digital voltage state.

In some preferred embodiments, a transducer may be used to detect a voltage change across a ciliary muscle. Eyelid and squinting movements may be sensed, for example, with optical sensors. Sensed data may be stored in memory and analyzed by a microprocessor to determine appropriate changes to the liquid meniscus lens.

In some embodiments, an intraocular lens system includes one or more antennae in an electrical zone 302. Antennae may be used, by way of non-limiting example, to receive radio frequency for charging power sources, for receiving data from other sensors, and for communication with external devices and other devices within an intraocular lens system. Antennae may be of various shapes and sizes within an electrical zone 302 of an intraocular lens system.

An intraocular lens system with liquid meniscus lens may be modified in two different ways: focus and adjustment. Its primary purpose is to change focus, accommodating distance vision, near vision, and intermediate vision. In some embodiments, changes in focus are automated, such as, for example, when a pressure transducer senses contraction of the capsular bag, and a processor in the intraocular lens system translates the magnitude of capsular bag pressure into a corresponding optical power change within the liquid meniscus lens. In other embodiments, changes in focus may be controlled manually, such as, for example, when a wearer presses a button on a fob, transmitting a command to a processor in an intraocular lens system which in turn initiates an optical power change within a liquid meniscus lens.

Adjustment refers to one-time or ad-hoc modification of an intraocular lens system. Adjustment may, for example, set or modify the diopter change between far and near vision, may program operation of a liquid meniscus lens to correct for a specific degree and magnitude of astigmatism, and may change the sensitivity of the intraocular lens system to changes in a ciliary muscle or capsular bag. Adjustment may be accomplished by an eye care professional before an intraocular lens system is surgically implanted or after implantation. In some embodiments, post-surgical adjustment may be via a device which allows the input or setting of parameters and the transmission of parameters to the intraocular lens. In some embodiments, the patient may participate in or control post-surgical adjustment in order to fine-tune vision settings. In some embodiments, default optical characteristics will provide optical correction for a "distant" vision correction and post surgical adjustment will modify one or more optical characteristics of "near" vision. However, it is within the scope of this invention to optical characteristics of both distant and near vision states of a multi-state intraocular lens.

Modifications for focus and adjustment may be independent for each intraocular lens system, or may be coordinated between intraocular lens systems worn in both eyes. For example, in some implementations it may be desirable for focus for both eyes to be determined based on sensed data from one eye. In other situations, it may be optimal for focus to be independently managed by each intraocular lens system.

Figure 4:
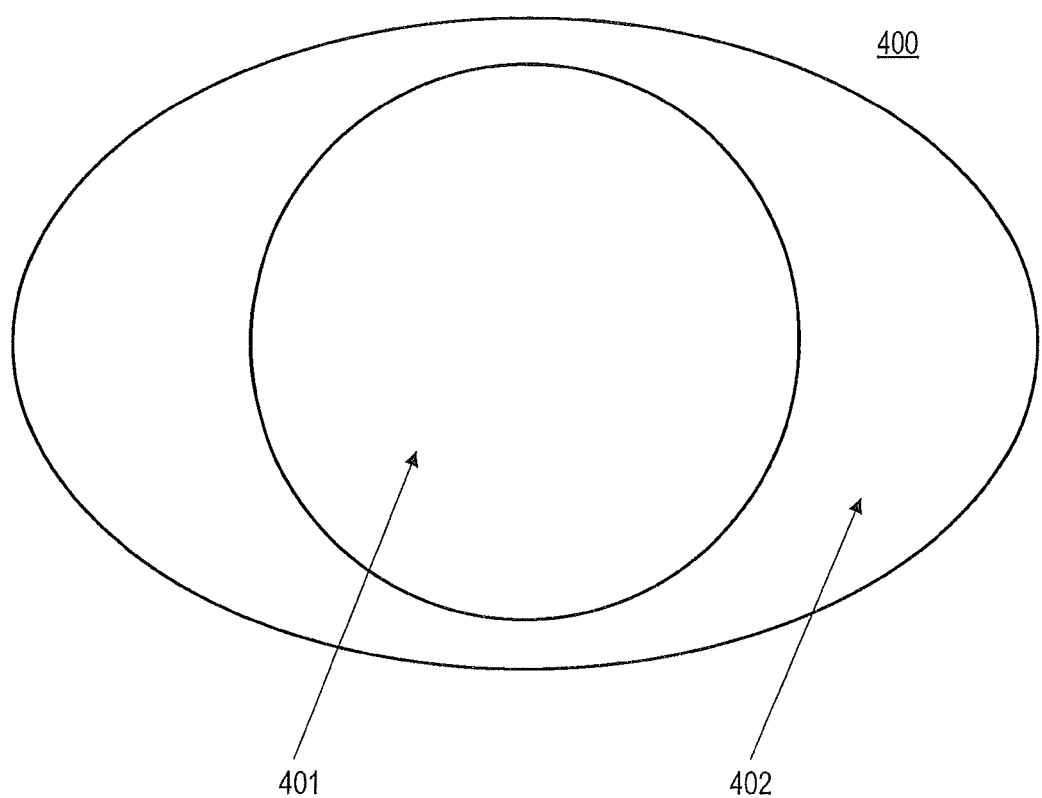
FIG. 4 illustrates a front view block diagram of an exemplary intraocular lens system in the form of an ellipse according to some embodiments of the present invention.

Referring now to FIG. 4, an exemplary intraocular lens system is depicted in a front view block diagram. This embodiment features an intraocular lens system 400 in elliptical form, including a circular visual zone 401 surrounded by an electrical zone 402. Other embodiments may include an optical zone 401 of elliptical, rectangular, or other shape conducive to vision correction. In the present invention, the visual zone 401 consists of a liquid meniscus lens. A liquid meniscus lens may be in a traditional "hockey puck" form, as shown in FIGS. 1A and 1B, or in an arcuate form, as shown in FIG. 2.

The intraocular lens system of FIG. 4 includes the same features and capabilities as the intraocular lens system described in FIG. 3, such as, for example, ability to change focus, adjustability of settings, electrical zone elements, power management subsystem, charging options, folding capability and encapsulation.

Figure 5:
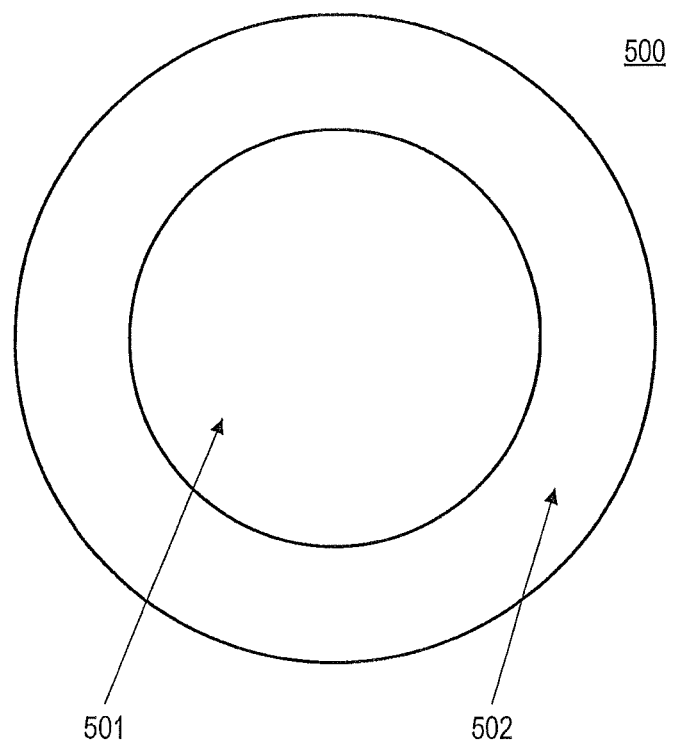
FIG. 5 illustrates a front view block diagram of an exemplary intraocular lens system in the form of a circle according to some embodiments of the present invention.

Referring now to FIG. 5, an intraocular lens system 500 is depicted in a front view block diagram. In this embodiment, the intraocular lens system 500 is in the form of a circle with a circular visual zone 501 surrounded by an electrical zone 502. Other embodiments may include an optical zone 501 of elliptical, rectangular, or other shape conducive to vision correction. In the present invention, the visual zone 501 consists of a liquid meniscus lens. A liquid meniscus lens may be in a traditional "hockey puck" form, as shown in FIGS. 1A and 1B, or in an arcuate form, as shown in FIG. 2.

The intraocular lens system of FIG. 5 includes the same features and capabilities as the intraocular lens system described in FIG. 3, such as, for example, ability to change focus, adjustability of settings, electrical zone elements, power management subsystem, charging options, folding capability and encapsulation.

Referring now to FIG. 6, three cross sectional side views of non-limiting exemplary intraocular lens systems are depicted. FIG. 6A shows an embodiment in which an intraocular lens system is flat. An arcuate version of an intraocular lens system is depicted in FIG. 6B. An arcuate intraocular lens system may be placed convex toward the exterior of the eye, or convex toward the interior of the eye. FIG. 6C depicts a biconvex intraocular lens system. FIGS. 6A, 6B and 6C are intended to depict possible embodiments, but do not limit the scope of the invention as other variations in shape are possible.

What is claimed is:

1. An implantable intraocular lens system comprising an optical zone and an electrical zone adjacent thereto, wherein:
   the optical zone comprises:
      a single continuous front curve lens comprising a front curve lens exterior surface and a front curve lens interior surface;
      a single continuous back curve lens comprising a back curve lens interior surface and a back curve lens exterior surface, said back curve lens is secured to said front curve lens such that said front curve lens interior surface and said back curve lens interior surface form a cavity therebetween, said front curve lens and said back curve lens of size and shape to replace an intraocular lens in a human eye;
      a volume of oil and a volume of saline solution contained within the cavity with a meniscus formed between said volume of oil and said volume of saline solution, wherein said meniscus comprises an optical characteristic; and
      a conductive coating consisting of a first conductive material directly on at least a perimeter area of one or both of said front curve lens interior surface and said back curve lens interior surface; and
   the electrical zone comprises a power source for applying an electrical charge to the conductive coating, wherein the application of the electrical charge causes a change of the optical characteristic of said meniscus.

2. The implantable intraocular lens system of claim 1 additionally comprising a microprocessor positioned in the electrical zone proximate to the front curve lens and the back curve lens, said microprocessor in electrical communication with the power source to control the application of the electrical charge to the conductive coating.

3. The implantable intraocular lens system of claim 1 additionally comprising an adhesive securing said front curve lens to the back curve lens, wherein at least one of said front curve lens exterior surface and said back curve lens exterior surface comprises an arcuate shape.

4. The implantable intraocular lens system of claim 3 wherein both of said front curve lens exterior surface and said back curve lens exterior surface comprise arcuate shapes.

5. The implantable intraocular lens system of claim 3 wherein the front curve lens exterior surface comprises an optical power other than 0 diopters.

6. The implantable intraocular lens system of claim 3 wherein the front curve lens interior surface comprises an optical power other than 0 diopters.

7. The implantable intraocular lens system of claim 3 wherein the back curve lens interior surface comprises an optical power other than 0 diopters.

8. The implantable intraocular lens system of claim 1 wherein the power source comprises a battery.

9. The implantable intraocular lens of claim 1 additionally comprising a wireless transmitter for communicating logic to and from a microprocessor.

10. The implantable intraocular lens system of claim 9 wherein the communicated logic modifies a focus of the optical characteristic formed by the meniscus.

11. The implantable intraocular lens system of claim 10 wherein the volume of oil is less than the volume of saline solution contained within the cavity.

12. The implantable intraocular lens system of claim 11 wherein the volume of oil is 66% or more of the volume of saline solution.

13. The implantable intraocular lens system of claim 12 wherein the electrical charge comprises a direct current.

14. The implantable intraocular lens system of claim 13 wherein the electrical charge is 20.0 volts.

15. The implantable intraocular lens system of claim 13 wherein the electrical charge is between 18.0 volts to 22.0 volts.

16. The implantable intraocular lens system of claim 13 wherein the electrical charge is 5.0 volts.

17. The implantable intraocular lens system of claim 13 wherein the electrical charge is between 3.5 volts to 7.5 volts.

18. The implantable intraocular lens system of claim 11 wherein the volume of oil is 90% or less of the volume of saline solution.

19. The implantable intraocular lens system of claim 18 wherein the conductive coating extends from an area internal to the cavity to an area external to the cavity.

20. The implantable intraocular lens system of claim 19 wherein the conductive coating which extends to the area external to the cavity forms an electrical terminal for providing the electrical charge to the conductive coating based upon a signal from the microprocessor.

21. The implantable intraocular lens system of claim 19 additionally comprising a channel through one or both of the front curve lens and the back curve lens and a second conductive material filling the channel.

22. The implantable intraocular lens system of claim 21 additionally comprising a terminal in electrical communication with the second conductive material filling the channel.

23. The implantable intraocular lens system of claim 22 wherein the application of the electrical charge to the terminal causes a change in an arcuate shape of the meniscus.

24. The implantable intraocular lens system of claim 19 additionally comprising an insulator coating along at least a second portion of the interior surface of the front curve lens, wherein the insulator coating comprises an electrical insulator.

25. The implantable intraocular lens system of claim 24 wherein the insulator coating comprises a boundary area to maintain separation between the conductive coating and the volume of saline solution contained in the cavity between the front curve lens and the back curve lens.

26. The implantable intraocular lens of claim 1, wherein the conductive coating is directly on the perimeter area of both of said front curve lens interior surface and said back curve lens interior surface.

27. An implantable intraocular lens system comprising an optical zone and an electrical zone adjacent thereto, wherein:
the optical zone comprises:
   a single continuous front curve lens comprising a front curve lens exterior surface and a front curve lens interior surface;
   a single continuous back curve lens comprising a back curve lens interior surface and a back curve lens exterior surface, said back curve lens positioned proximate to said front curve lens such that said front curve lens interior surface and said back curve lens interior surface form a cavity therebetween, said front curve lens and said back curve lens of size and shape to replace an intraocular lens in a human eye;
   a volume of oil and a volume of saline solution contained within the cavity with a meniscus formed between said volume of oil and said volume of saline solution, wherein said meniscus comprises an optical characteristic; and
   a conductive coating consisting of a first conductive material directly on at least a perimeter area of one or both of said front curve lens interior surface and said back curve lens interior surface;
wherein the electrical zone comprises a power source for applying an electrical charge to the conductive coating, wherein the application of the electrical charge causes a change of the optical characteristic of said meniscus; and
wherein the meniscus resides only on the front curve lens interior surface.

28. An implantable intraocular lens system comprising an optical zone and an electrical zone adjacent thereto, wherein:
the optical zone comprises:
   a single continuous front curve lens comprising a front curve lens exterior surface and a front curve lens interior surface;
   a single continuous back curve lens comprising a back curve lens interior surface and a back curve lens exterior surface, said back curve lens positioned proximate to said front curve lens such that said front curve lens interior surface and said back curve lens interior surface form a cavity therebetween, said front curve lens and said back curve lens of size and shape to replace an intraocular lens in a human eye;
   a volume of oil and a volume of saline solution contained within the cavity with a meniscus formed between said volume of oil and said volume of saline solution, wherein said meniscus comprises an optical characteristic; and
   a conductive coating consisting of a first conductive material directly on at least a perimeter area of one or both of said front curve lens interior surface and said back curve lens interior surface; and
wherein the electrical zone comprises a power source for applying an electrical charge to the conductive coating, wherein the application of the electrical charge causes a change of the optical characteristic of said meniscus; and
wherein the cavity is formed by only the front curve lens interior surface and the back curve lens interior surface.

* * * * *